United States Patent [19]

Noell

[11] Patent Number: 4,968,839

[45] Date of Patent: Nov. 6, 1990

[54] SYNTHETIC PROCESS FOR THE PREPARATION OF N,N DIMETHYL GLYCINE (DMG)

[75] Inventor: C. Wayne Noell, Tucson, Ariz.

[73] Assignee: Foodscience Corporation, Essex Junction, Vt.

[21] Appl. No.: 395,149

[22] Filed: Aug. 16, 1989

Related U.S. Application Data

[63] Continuation-in-part of Ser. No. 170,873, Mar. 21, 1988, abandoned.

[51] Int. Cl.$^5$ ............................................. C07C 229/00
[52] U.S. Cl. .................................................... 562/575
[58] Field of Search ......................................... 562/575

[56] References Cited

U.S. PATENT DOCUMENTS 2,479,942  8/1949  Lecher et al. ..................... 558/452
3,714,223  1/1973  Godfrey et al. ..................... 558/346

*Primary Examiner*—Michael L. Shippen
*Attorney, Agent, or Firm*—Victor Flores

[57] ABSTRACT

A process for synthetically producing N,N-Dimethyl Glycine, commonly referred to as DMG, through the neutralization of N,N-dimethyl glycine sodium salt with sulfuric acid wherein the N,N-dimethyl glycine sodium salt is prepared by reacting formaldehyde, sodium bisulfite, dimethyl amine, and sodium cyanide followed by agitation with caustic soda beads. Through the preparation and intermediate steam distillation and isolation of N,N-Dimethylamino acetonitrile. The nitrile solution is subjected to caustic hydrolysis then is subsequently neutralized leaving DMG in methanol extraction solvent. The methanol is removed in an azeotropic distillation step to produce DMG in a high yield, low cost and excellent quality.

1 Claim, 3 Drawing Sheets

SYNTHETIC PROCESS FOR THE PREPARATION OF N,N DIMETHYL GLYCINE (DMG)

This is a continuation-in-part of co-pending application Ser. No. 170,873 filed on Mar. 21, 1988, now abandoned.

FIELD OF THE INVENTION

This invention relates to a new and useful synthetic method for the preparation of N,N-dimethyl glycine (dmg). More particularly, the invention relates to a method of producing N,N-dimethyl glycine which employs substantially a two (2) step process resulting in higher product yield and lower raw material costs than prior art synthetic methods.

DESCRIPTION OF THE PRIOR ART

N,N-dimethyl glycine has previously been synthesized utilizing monochloro acetic acid (A) as a starting material. Treatment of monochloro acetic acid (A) with aqueous dimethyl amine followed by hydrochloric acid yields N,N-dimethyl glycine as its hydrochloride salt.

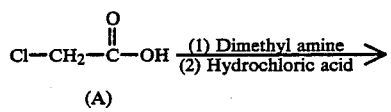
(A)

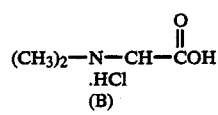
(B)

The yield of quality product by this method is 50%. The N,N-dimethyl glycine hydrochloride salt (B) is then converted to its free base form (C) through the use of expensive ion exchange resins which must be periodically replaced.

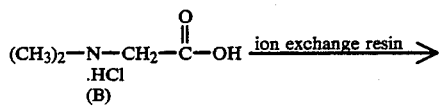
(B)

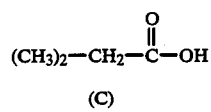
(C)

The chemical raw material cost by this process is approximately $40 for every kilogram of N,N-dimethyl glycine produced. The yield of quality product produced by this method is approximately 50%.

No other process for producing dmg, other than the above mentioned process that requires N,N-dimethyl glycine hydrochloride salt to be further processed using ion exchange resins to produce dmg, is known to exist. This sole known, low-yield process for producing dmg and associated high costs due to the use of ion exchange resins has led to query the possibility of producing dmg using other chemical formulations. While known chemical formulations, such as those taught by U.S. Pat. No. 3,714,223 for use in the production of diethylamino acetonitrile, provide a means for production of an intermediate solution, namely dimethylamino acetonitrile, that could be further processed to produce dmg, such intermediate chemical formulations have not been developed, commercially or otherwise, for the production of dmg. The chemical formulation, having potential for producing an intermediate solution of dmg, produces diethylamino acetonitrile ($E_1$) through reaction of diethylamine ($A_1$), sodium cyanide (B), formaldehyde (C), and sodium bisulfite (D) according to the following formula:

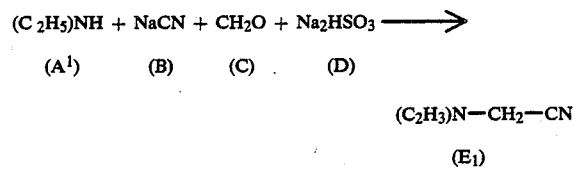

This diethylamino acetonitrile chemical formulation, upon utilizing dimethylamine instead of diethylamine, can produce dimethylamino acetonitrile, which is recognized as an intermediate solution of dmg. However, notwithstanding the apparent ease of producing the intermediate solution of dmg, namely dimethylamino acetonitrile, according to the diethylamino acetonitrile chemical formulation, dmg is only known to be produced according to the sole known process as discussed above. It is believed that if the diethylamino acetonitrile chemical formulation were utilized to produce the intermediate solution, namely dimethylamino acetonitrile, dmg could be produced with higher yields and lower production costs by further processing the dimethylamino acetonitrile through a subsequent chemical process, (which, according to the present invention involve steam distillation, caustic soda hydrolysis, neutralization using sulfuric acid and a series of purification, filtration and distillation steps), that is less expensive than the present use of ion exchange resins to produce dmg when utilizing monochloro acetic acid as a starting material.

Thus, the presently known commercial process for producing dmg, which concerns the treatment of monochloro acetic acid with aqueous dimethylamine followed by hydrochloric acid to yield N,N-dimethyl glycine hydrochloride salt and which must be further processed using ion exchange resin to produce dmg, is considered expensive due to the ion exchange resin process step to produce free base dmg. Also, although other intermediate chemical formulations could have been used to produce dmg, i.e. such as the chemical formulation process for producing diethylamino acetonitrile, there are no known processes that have capitalized on this potential to produce the dmg intermediate chemical solution, i.e. dimethylamino acetonitrile, which can be further processed to produce dmg. Therefore, the need for commercially efficient and low cost means of producing N,N-dimethyl glycine is seen to be needed.

SUMMARY OF THE INVENTION

Accordingly, a primary object of the invention is to provide a process which synthesizes N,N-dimethyl glycine and achieves high quality product yield at a nominal cost. Another object of the invention is to synthetically produce N,N-dimethyl glycine using, in a first reaction stage, using principles of a known synthetic process which produces diethylamino acetonitrile.

Accordingly, the present invention thus provides a process whereby the aforementioned objects are satisfied and thus, relates to a process wherein dimethylamine, sodium cyanide, formaldehyde and sodium bisulfite are reacted to form dimethylamino acetonitrile which is purified through steam distillation. Upon distillation the aqueous distillate is then subjected to caustic soda hydrolysis which results in production of the sodium salt of N,N-dimethyl glycine as a crystalline white product in 80% yield. The N,N-dimethyl glycine sodium salt is then neutralized using sulfuric acid. After a series of purification, filtration and distillation steps, the pure desired product, N,N-dimethyl glycine (dmg), results as a white crystalline product in 66% yield from the sodium salt of dmg. The process comprises a reaction according to the formula:

(A)    (B)    (C)    (D)

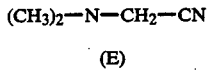

(E)

which produces an aqueous distillate of dimethylamino acetonitrile, (E), in good yield. The aqueous distillate is then subjected to caustic soda hydrolysis to form a sodium salt of dmg which is subsequently neutralized to 80% yield of the free base of dmg according to the following formula:

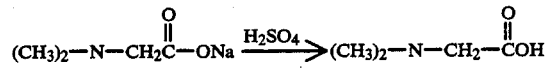

DETAILED DESCRIPTION OF THE INVENTION

Upon substituting dimethylamine for diethylamine in the prior art process reaction formula, the desired dimethylamino acetonitrile was obtained as a satisfactory starting point of the present invention. Through experiment it was determined that steam distillation of the reaction mass gave the desired product which when subjected to caustic soda hydrolysis would produce a high yield of the salt of dmg. Although calcium hydroxide and potassium hydroxide may be used to obtain the salt of dmg, they were found ineffective when compared to the use of sodium hydroxide in the hydrolysis step. The sodium hydroxide results in an easier isolation of the sodium salt and was found to produce a higher yield and higher quality dmg sodium salt.

In the final step for producing dmg, the salt of dmg must be neutralized. Although the use of hydrochloric acid may achieve the desired results, it was determined that the product was contaminated with sodium chloride and may not be an adequate acid in the neutralization process. Through experiment it was found that the use of sulfuric acid allowed easy purification and separation. Although requiring repeated filtration and use of anhydrous sodium sulfate, dmg is produced in a totally anhydrous form in methanol, the extraction solvent.

After distillation of the methanol and a further azeotropic distillation to rid the final traces of methanol a final product suspended in isopropyl alcohol is produced. Upon cooling filtering and dry dmg is produced.

In order to better illustrate the invention a practical example of a preferred embodiment is reported herewith. The protocol is simply illustrative and must not be intended as a limitation of the invention claimed hereby.

EXAMPLE

Figure 1:
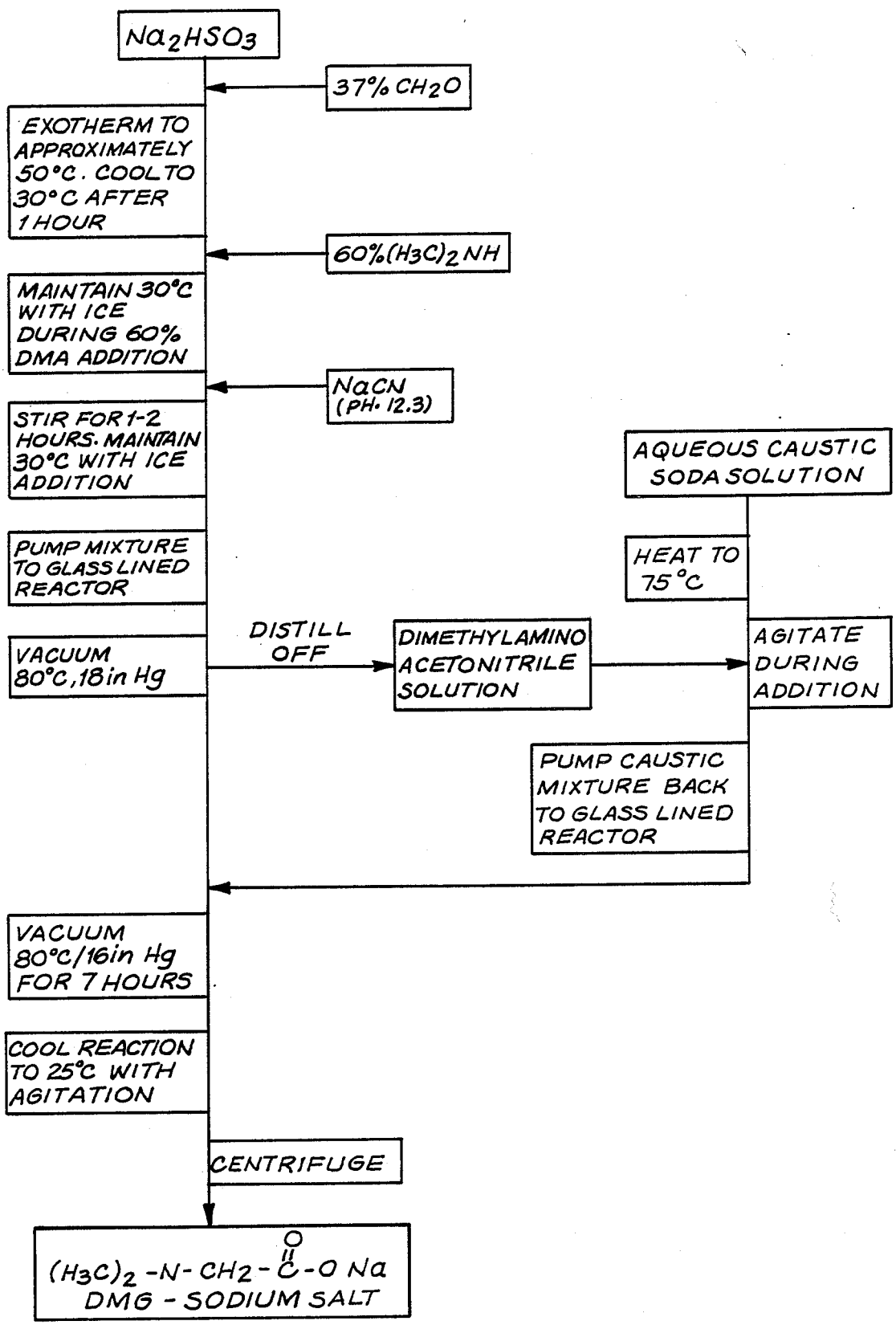
FIG. 1 shows in block diagram form the chemical reaction process for production of the sodium salt of dmg.

Referring now to FIG. 1, an aqueous solution of sodium bisulfite 458 LBS. (2000 moles) in 150 gallons of deionized water was made up in a 500 gallon tank with agitation and cooling coils. To the stirring bisulfite solution was added 357 lbs. (2000 moles) of 37% formaldehyde as rapidly as possible. The reaction mixture liberated heat and produced a solution 45 degrees C. and was stirred for one hour. The cooling coils were then utilized to maintain a solution temperature of 35 degrees C. At this point 331 lbs. (2000 moles) of 60% dimethyl amine solution was pumped into the stirring mixture in portions, with ice addition to maintain the reaction temperature at approximately 30 degrees C. The total volume was 330 gallons at this point, and stirring was continued for 30 minutes. Then a sodium cyanide solution 2000 lbs. (1867 moles) in 60 gallons of deionized water containing 2 lbs. of caustic soda beads to maintain pH of 12.5 was added in a steady stream over approximately 45 minutes. Ice was added to maintain the reaction temperature at 30 degrees C. The total volume at this point was approximately 430 gallons. After one hour of continued agitation the reaction mixture was transferred to a 500 gallon glass lined reactor. Still referring to FIG. 1 the reaction mixture was then distilled at 80 degrees C. steam jacket heating at 18 in. HG. until 180 gallons of distillate was obtained in a 200 gallon receiver tank. Approximately 4.5 hours was required for the 180 gallons of dimethylamino acetonitrile solution to distill and collect in the receiver tank. To the 500 gallon tank equipped with agitator and cooling coils was added 150 gallons of deionized water which was then agitated during the addition of 166 lbs. of caustic soda beads. During the mixing the temperature of the caustic solution rose to 45-50 degrees C and was subsequently raised to 75-80 degrees C. by steam coil heating. The 180 gallons of dimethylamino acetonitrile solution was pumped into the hot caustic mixture, at a rate such that the ammonia generated was easily handled by a spray water scrubber system. After all of the nitrile/water mixture had been added (approx. 2 hours) the reaction temperature was held for one hour longer at 75-80 degrees C. to complete the hydrolysis reaction. The hot caustic reaction mass was then pumped into the 500 gallon glass lined reactor system and distilled under reduced pressure at 16 in. HG. / 80 degrees C. for 7 hours. The reaction mass was then cooled to 25 degrees C. and the first crop of N,N-dimethyl glycine sodium salt was collected by filtration in a 1750 rpm centrifuge and stored in plastic as the damp product.

Repeating the appropriate steps shown in FIG. 1 the filtrate from the centrifuge was pumped back into the 500 gallon reactor and again stripped, as before, at 16 in. HG. / 80 degrees C. for 4 hours. The mass was cooled to 25 degrees C. and filtered to obtain a second crop which was combined with the first crop. A third crop was obtained in a similar manner and combined with the first and second crops. The filtrate from the third crop was stored to be added to the next batch at the point of filtration of the N,N-dimethyl glycine sodium salt. The three combined damp crops of N,N-dimethyl glycine sodium salt weighed 430 lbs. (damp weight). At this point 3 more batches of N,N-dimethyl glycine sodium salt were run in identical procedure as just described above. The combined 4 batches (12 crops) of N,N-dimethyl glycine sodium salt (damp weight) gave 2122 lbs. The product contained 30% water content or 1632 lbs., dry weight. The melting point was 288 degrees C. and the reaction yield was 80%.

Figure 2:
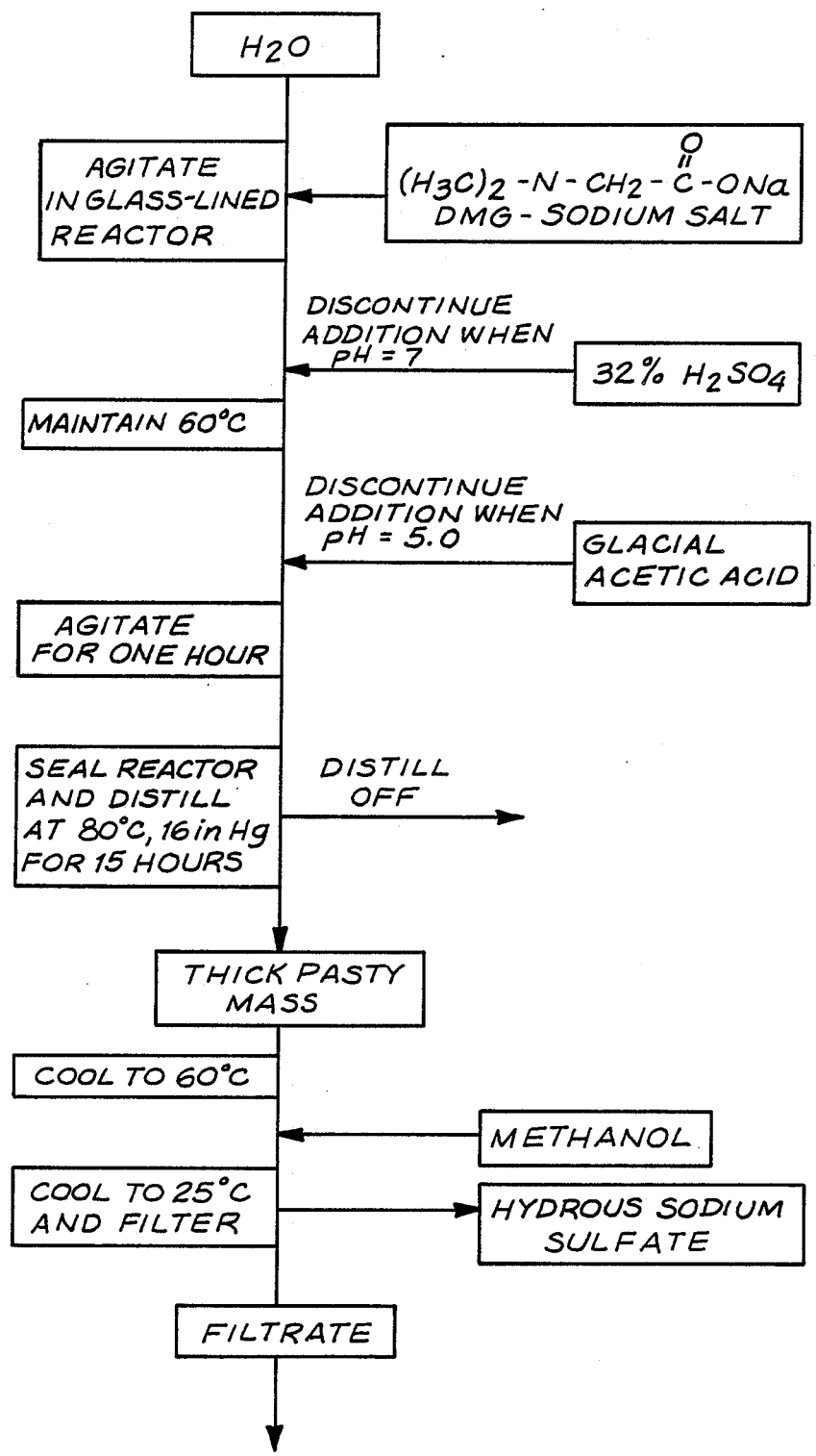
FIG. 2 shows a partial block diagram the neutralization of the salt of dmg to yield free base dmg.

Referring now to FIG. 2, a 500 gallon glass lined reactor was charged with 150 gallons of deionized water and the agitator turned on. The 2122 lbs. (damp weight) of N,N-dimethyl glycine sodium salt was added to the reactor. With continued agitation, a solution of 32% sulfuric acid (1918 lbs.) was added with jacket cooling maintaining the internal temperature below 60 degrees C. Toward the end of this neutralization procedure after approximately 1800 lbs. of acid had been added the addition of acid was slowed and the pH checked carefully. The addition was stopped at pH-7 and one gallon of glacial acetic acid was added to obtain a pH of 5.0. After one hour of continued agitation, a test for cyanide in the atmosphere inside of the reactor was positive at 22 ppm. The reactor was sealed and the mixture was distilled at reduced pressure (16 in. Hg/80 degrees C.) for 15 hours. A thick pasty mass remained in the reactor and it was jacket cooled to 60 degrees C. Then, 5 drums (290 gallons) of methanol were added to the reaction mixture. A test for cyanide at this point was negative. The mixture was then cooled to 25 degrees C. and filtered through a plate and frame filter to remove the glaubers salt (hydrous sodium sulfate).

Figure 3:
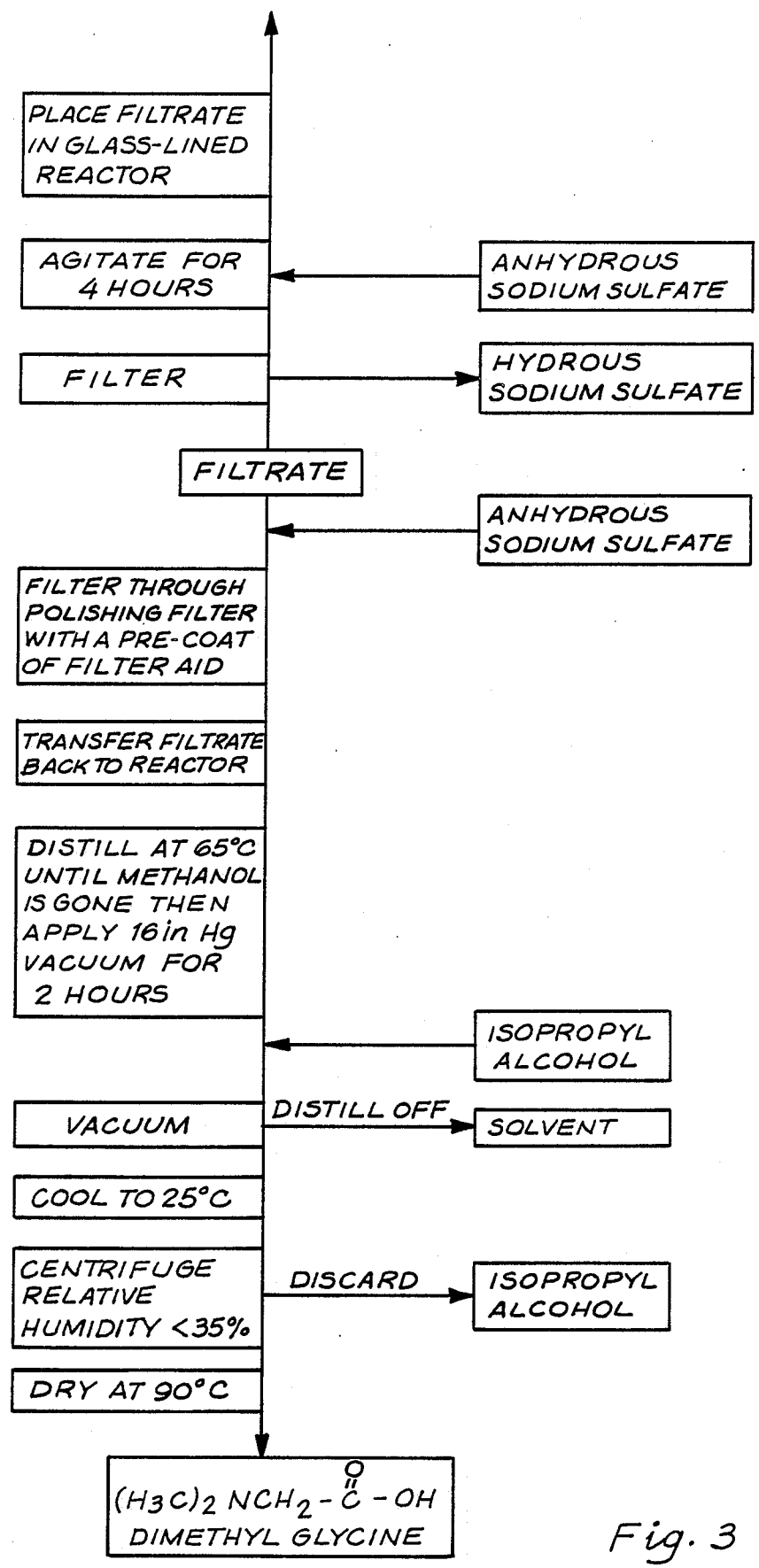
FIG. 3 shows in block diagram form the final azeotropic distillation to yield the final product, dmg.

Referring now to FIG. 3, the filtrate were then pumped back to the reactor and agitated as 300 lbs. of anhydrous sodium sulfate was added. Agitation was continued for 4 hours to dry the water from the mixture. The mass was again filtered through a plate and frame filter to again remove the hydrous sodium sulfate. The filtrate was again stirred with 30 lbs. of anhydrous sodium sulfate and filtered through a polishing filter having a pre-coat of a filtering aid. The filtrate was transferred back to the reactor and distilled at 65 degrees C. until no more methanol would distill. Then a vacuum of 16 in. Hg was applied for 2 hours. Six (6) drums (324 gallons) of anhydrous isopropyl alcohol were added to the remaining mass and again distilled to remove one drum of solvent. The stirring mass was then cooled to 25 degrees C. and the product was collected in a centrifuge, with a small isopropyl alcohol wash. This filtration was carried out in an atmosphere where the relative humidity was less than 45%, preferably at 35% or less. The product was then dried in poly-lined trays under vacuum at 90 degrees C. The dried product was ground, packaged and stored in plastic containers. The yield of N,N-dimethyl glycine was 402 kg. (66%). The melting point of the product was 181–3 degrees C.

While the invention has been particularly shown and described with reference to preferred embodiments thereof, it will be understood by those skilled in the art that the foregoing and other changes in forms and details may be made therein without departing from the spirit and scope of the invention.

What is claimed is:

1. A process for producing N,N-dimethyl glycine, comprising the steps of:
   (a) forming a first mixture by reacting aqueous sodium bisulfite with aqueous formaldehyde having a concentration of 37 wt. percent and cooling said resulting first mixture to a temperature of about 35 degrees centigrade, the mole ratio of said sodium bisulfite to said formaldehyde being 1:1;
   (b) forming a second mixture by reacting said first mixture with an aqueous dimethylamine solution having a concentration of 60 wt. percent and cooling said resulting second mixture to a temperature of about 30 degrees centigrade, the mole ratio of said dimethylamine solution to said sodium bisulfite and to said formaldehyde being 1:1;
   (c) forming a third mixture by reacting said second mixture with sodium cyanide and water containing sodium hydroxide to maintain a pH of about 12.3 to 12.5 and cooling said resulting third mixture to a temperature of about 30 degrees centigrade, the mole ratio of said sodium cyanide to said dimethylamine solution, to said sodium bisulfite and to said formaldehyde being 1:0.934;
   (d) transferring said third mixture to a reactor, after being agitated for about 60 minutes, and separating and recovering from said third mixture a dimethylamino acetonitrile solution, said separation being by steam distilation into a receiver container;
   (e) forming a fourth mixture by reacting said recovered dimethylamino acetonitrile with a mixture of water and sodium hydroxide heated to about 75 to 80 degrees centigrade, said resulting fourth mixture being maintained at 75 to 80 degrees centigrade for about 60 minutes to complete the hydrolysis reaction;
   (f) transferring said fourth mixture to a reactor and separating and recovering N,N-dimethyl glycine sodium salt;
   (g) forming a fifth mixture by agitating said N,N-dimethyl glycine sodium salt in water to form an aqueous solution and reacting in a reactor said aqueous solution with sulfuric acid having a 32 weight per cent concentration for neutralizing said resulting fifth mixture, said fifth mixture being maintained at a temperature ranging of about 60 degrees during said neutralization to a pH of about 5.0;
   (h) separating said fifth mixture by distillation to recover a thick pasty mass;
   (i) forming a sixth mixture by reacting said thick pasty mass with methanol and cooling said resulting sixth mixture to a temperature of about 25 degrees centigrade;
   (j) separating said sixth mixture to recover a first filtrate and remove hydrous sodium sulfate during formation of said sixth mixture;
   (k) forming a seventh mixture by reacting said first filtrate in a reactor with anhydrous sodium sulfate, said seventh mixture being agitated for purposes of absorbing any remaining traces of water;
   (l) separating said seventh mixture to recover a second filtrate and remove hydrous sodium sulfate during formation of said seventh mixture;
   (m) transferring said second filtrate to a reactor and distilling to remove substantially all of said methanol leaving a residue;
   (n) forming an eight mixture by adding anhydrous isopropyl alcohol to said residue; and
   (o) separating said eight mixture by firstly, distilling to remove any remaining traces of said methanol, secondly, cooling to a temperature of about 25 degrees centigrade and thirdly, filtering to recover said N,N-dimethyl glycine.

* * * * *